United States Patent [19]

Callaghan

[11] Patent Number: 4,860,751
[45] Date of Patent: Aug. 29, 1989

[54] ACTIVITY SENSOR FOR PACEMAKER CONTROL
[75] Inventor: Frank J. Callaghan, Miami, Fla.
[73] Assignee: Cordis Corporation, Miami, Fla.
[21] Appl. No.: 697,919
[22] Filed: Feb. 4, 1985
[51] Int. Cl.⁴ .............................................. A61N 1/36
[52] U.S. Cl. ............................................. 128/419 PG
[58] Field of Search ..................... 128/419 D, 419 PG
[56] References Cited

U.S. PATENT DOCUMENTS

| 3,593,718 | 7/1971 | Krasner et al. | 128/419 PG |
|---|---|---|---|
| 3,650,277 | 3/1972 | Sjostrand et al. | 128/421 |
| 4,009,721 | 3/1977 | Alcidi | 128/419 PG |
| 4,140,132 | 2/1979 | Dahl | 128/419 PG |
| 4,201,219 | 5/1980 | Gonzalez et al. | 128/419 PG |
| 4,390,022 | 6/1983 | Calfee et al. | 128/419 PG |
| 4,404,972 | 9/1983 | Gordon et al. | 128/419 PG |
| 4,428,378 | 1/1984 | Anderson et al. | 128/419 PG |
| 4,467,807 | 8/1984 | Bornzin | 128/419 PG |
| 4,503,857 | 3/1985 | Boute et al. | 128/419 PG |
| 4,527,568 | 7/1985 | Rickards | 128/419 PG |
| 4,535,774 | 8/1985 | Olson | 128/419 PG |
| 4,543,954 | 10/1985 | Cook et al. | 128/419 PG |

Primary Examiner—William E. Kamm
Attorney, Agent, or Firm—Gerstman & Ellis

[57] ABSTRACT

A cardiac pacer is provided which incorporates a sensor responsive to the physical activity of the pacer-wearing patient. The output of the physical activity sensor is utilized by control circuitry of a physiological sensor to enable the physiological sensor to monitor a selected physiological parameter only if the physical activity of the pacer-wearing patient exceeds a selected threshold. In this manner, the electrical energy requirements of the pacer are lessened.

18 Claims, 3 Drawing Sheets

U.S. Patent   Aug. 29, 1989   Sheet 1 of 3   4,860,751
FIG. 1
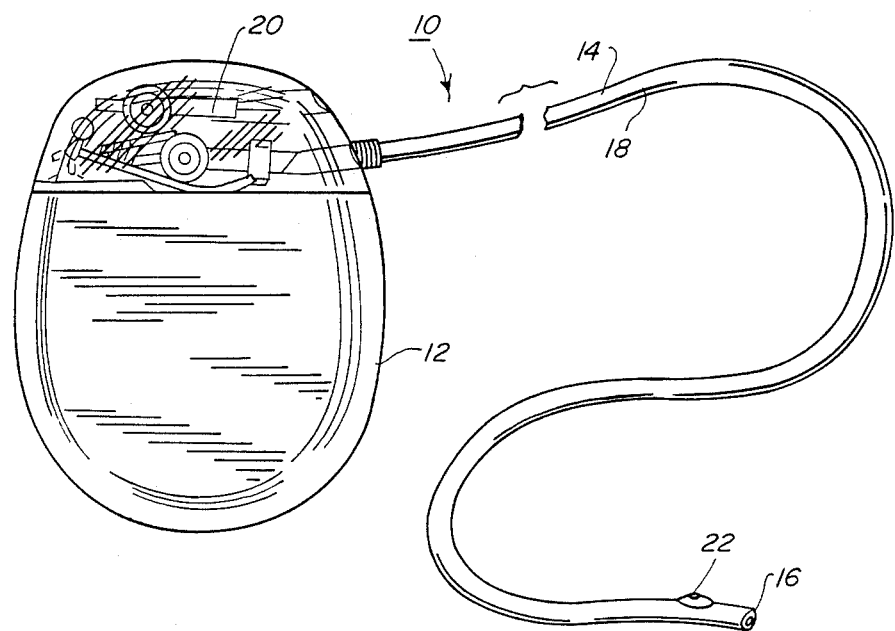
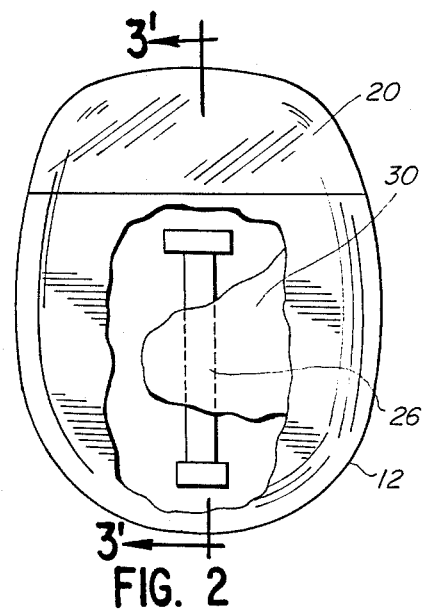
FIG. 2
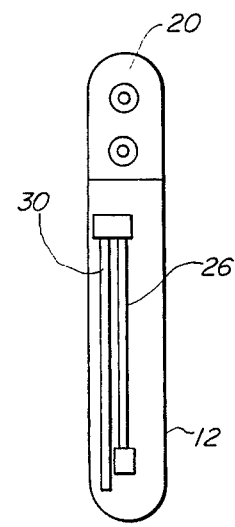
FIG. 3

ACTIVITY SENSOR FOR PACEMAKER CONTROL

BACKGROUND OF THE INVENTION

The present invention concerns a novel cardiac pacing system, and more particularly, a cardiac pacing system which is responsive to physiological requirements of the body.

Presently, activity-type cardiac pulse generators, namely, cardiac pacers, fall into three major categories.

The first category comprises those cardiac pacers whose output is generally controlled by the patient's or wearer's own cardiac rate. A base or minimum rate is programmed by the physician. When the patient's cardiac rate (either atrial or ventricular or both) decreases below this minimum programmed rate, the output of the cardiac pacer is suppressed. This is not a "true" activity pacer because only the cardiac electrical events dictate the rates or the escape interval of the implanted cardiac pacer. The "escape interval" is the time, usually in milliseconds, between successive output pulses of the cardiac pulse generator. An increase in the escape interval results in a decrease in rate. Conversely, a decrease in escape interval is an increase in rate.

The second category includes those cardiac pacers which have an activity sensor, the output of which determines the escape interval of the cardiac pulse generator. Increased physical activity of the patient will activate the sensor. The output of the sensor will provide a decrease in the escape interval or an increase in the rate of the stimulating of the cardiac muscle. As the patient's physical activity decreases, the escape interval will increase to some programmed level. Examples of this category are disclosed in U.S. Pat. Nos. 4,140,132 and 4,428,378.

The third category includes cardiac pacemakers which, as a part of the system, incorporate a physiological sensor such as one to measure the oxygen level of the pH level of the blood. Control circuitry which may include a microprocessor based on input from the physiological sensor dictates the escape interval changes. In this configuration, the physiological sensor requires current from the batteries to remain "on" at all times to monitor the physiological parameter chosen for measurement. This imposes a continuous drain on the batteries used to power the implantable pulse generator in addition the electrical energy required for sensing cardiac electrical events and emitting pulses to stimulate the cardiac muscle. An example of this category is disclosed in U.S. Pat. No. 4,467,807.

However, such physiological sensors are considered desirable for true physiological pacing or "closed loop" pacing. While such cardiac pacers have the advantage of being responsive to physiological requirements of the body (for example, the need for an increase in oxygen, the need to decrease carbon dioxide, the need to change pH level, etc.), they have the disadvantage of placing an increased energy demand on the batteries.

It is, therefore, an object of the present invention to provide a physiological sensitive cardiac pacer which does not have the disadvantage of placing a substantially increased energy demand on the batteries.

Another object of the present invention is to provide a physiologically sensitive cardiac pacer that is relatively simple in construction and easy to manufacture.

Other objects and advantages of the present invention will become apparent as the description proceeds.

BRIEF DESCRIPTION OF THE INVENTION

In accordance with the present invention, a cardiac pacing system is provided which comprises an implantable pacer and means for sensing the physical activity of the pacer-wearing patient. A physical activity threshold detector is coupled to the physical activity sensing means. Means are provided for sensing a selected physiological parameter of the patient and means are provided for controlling the operation of the physiological parameter sensing means in response to detection of a physical activity threshold by the physical activity threshold detector. In this manner, the energy required to power the physiological parameter sensing means is not enabled unless the physical activity sensed by the physical activity sensing means exceeds a selected threshold.

In the illustrative embodiment, the implantable pacer includes a sense amplifier for receiving sensed cardiac signals and pulse rate and timing means. The physical activity sensing means comprises a passive member carried by the implantable pacer, such as a piezoelectric element that requires no power to render it operational. The piezoelectric element is operable to generate a signal response to physical activity of the pacer-wearing patient.

In the illustrative embodiment, the physical activity threshold detector is programmed for operational control at a selected threshold of physical activity, and signal conditioning means couple the passive member for sensing physical activity to the physical activity threshold detector.

In the illustrative embodiment, the physiological parameter sensing means is adapted to sense a physiological parameter from one or more of the group consisting of the partial pressure of oxygen ($pO_2$), blood pressure, core temperature, $CO_2$ and $pCO_2$, $O_2$ in addition to $pO_2$, pH, respiration rate, respiration depth, and ventricular volume.

In accordance with one embodiment of the present invention, a cardiac pacing process is provided which comprises the steps of providing an implantable pacer; sensing the physical activity of the pacer-wearing patient; sensing a selected physiological parameter of the patient; detecting a selected threshold of the patient's physical activity; and controlling the physiological sensing in response to detection of the selected physical activity threshold.

A more detailed explanation of the invention is provided in the following description and claims, and is illustrated in the accompanying drawings.

BRIEF DESCRIPTION OF THE DRAWINGS

FIG. 1 is an elevational view of a cardiac pacing system constructed in accordance with the principles of the present invention;

FIG. 2 is an elevational view, partially broken for clarity, of the cardiac pacer of FIG. 1 showing the activity sensor positioned within the pacer;

FIG. 3 is a cross-sectional view thereof, taken along the line 3—3 of FIG. 2;

DETAILED DESCRIPTION OF THE ILLUSTRATIVE EMBODIMENT

Figure 4:
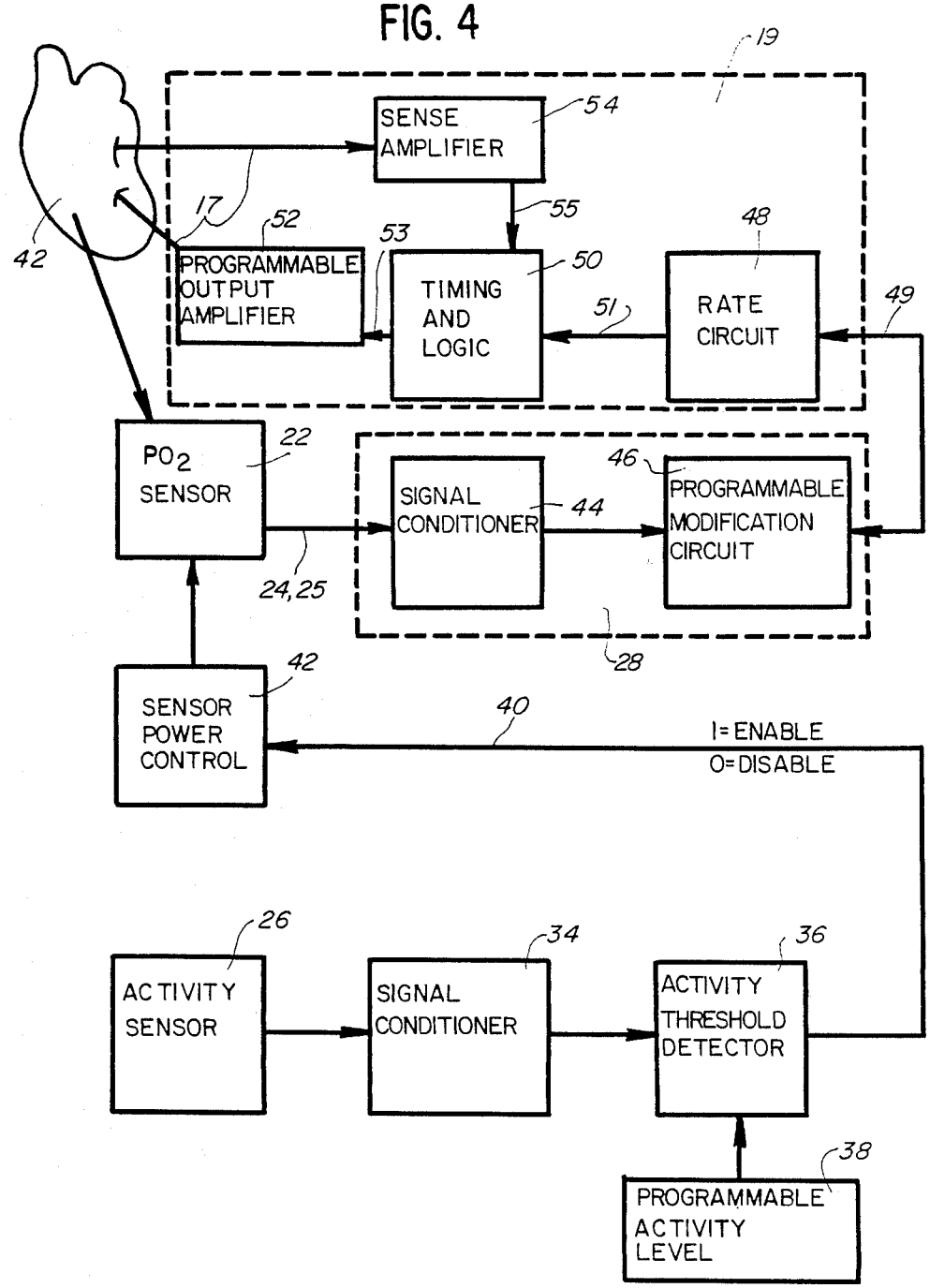
FIG. 4 is a block diagram of a cardiac pacer system in accordance with the principles of the present invention.

As stated above, in some prior art cardiac pacing systems, the output of an activity sensor directly controls the escape interval of an implanted cardiac pacer. In prior art types of cardiac pacing systems which incorporate a physiological sensor, battery power is necessary to maintain the sensor in the active state. This power constitutes an additional drain on the batteries thereby reducing the useful life of the implantable cardiac pacer.

In the present invention, referring to FIGS. 1–3 and 5, a cardiac pacing system 10 is provided comprising an implantable cardiac pacer 12 having connected thereto a pervenous lead 14. Lead 14 has an electrode 16 at its distal end for stimulating ventricular cardiac muscle and for sensing ventricular electrical activity. The electrical activity is transmitted through an insulated helical wire 17 (FIG. 5) located within the body 18 of the pervenous lead 14. The helical wire 17 forms a connection with the pacer circuitry 19 (FIG. 5) through the neck 20 of the pacer 12.

On the pervenous lead 14, exposed to the blood, is a sensor 22 which measures the partial pressure of oxygen ($pO_2$). The current needed to maintain the sensor 22 "on" and also to carry the information signal with respect to the $pO_2$ status is carried by two insulated wires 24, 25 (FIG. 5) which are contained within the pervenous lead body 18.

Figure 5:
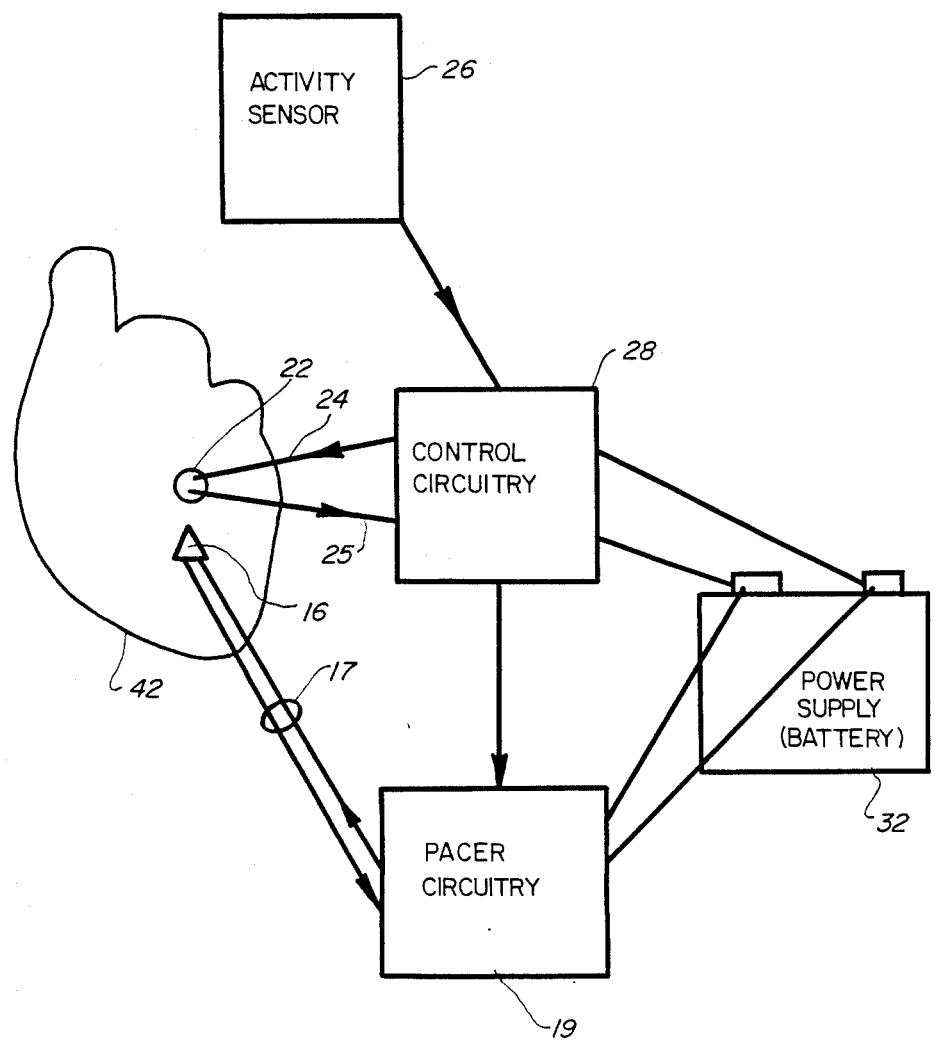
FIG. 5 is a diagram illustrating the interrelationship of the activity sensor and the physiological sensor with their related circuit elements.

Within the pacer 12 is a cantilevered suspended element 26 which constitutes a high impedance voltage generator such as a piezoelectric element. The output of piezoelectric element 26 is connected to a control circuit 28 of the main electronic circuit 30 contained within the cardiac pacer 12. Wires 24, 25 from the $pO_2$ sensor 22 are coupled to control circuitry 28 through the pacer neck 20. Power to both the control circuit 28 and the pacing/sensing circuit 19 is supplied by a battery 32 (FIG. 5). The piezoelectric element 26 is a passive element or sensor requiring no power to cause it to be operational. The distortion of the surface of or of the element 26 itself generates the appropriate signal.

Referring to FIG. 4, it can be seen that activity sensor 26, such as a piezoelectric element, is coupled to a signal conditioning circuit 34 which is coupled to an activity threshold detector 36. Activity threshold detector 36 is set to a selected activity level by programmable activity level 38. The output of activity threshold detector 36 is in binary form and may be a binary 1 if a threshold level of activity is sensed and a binary 0 if less than the threshold level of activity is sensed. The binary signal is fed via line 40 to a sensor power control circuit 42, which operates to power the $pO_2$ sensor 22 and the control circuit 28 only when a binary 1 signal is present on line 40. Control circuitry 28 includes signal conditioner 44 and programmable modification circuit 46. The signal conditioner 44 is coupled to the output of the $pO_2$ sensor 22 and the programmable modification circuit is coupled to the output of the signal conditioner 44. The pacer circuitry 19 includes a rate circuit 48 coupled via line 49 to the output of programmable modification circuit 46, a timing and logic circuit 50 coupled via line 51 to the output of rate circuit 48, a progammable output amplifier 52 coupled via line 53 to the output of timing and logic circuit 50, and a sense amplifier 54, the input of which is connected to helical wire 17 of lead 14 and the output of which is connected via line 55 to an input of timing and logic circuit 50.

When the patient is sedentary, there is no force on or movement of the piezoelectric element 26. Cardiac pacing of the ventricle continues in the usual fashion. Thus there is stimulation at a programmed fixed rate if the patient's own ventricular rate drops below the programmed rate, or if the patient's ventricular rate exceeds the programmed fixed rate there is no pacer output.

If the patient becomes physically active, such as by walking or climbing stairs, movement of the body results in distortion or movement of the piezoelectric element 26. The signal generated by the movement of the piezoelectric element 26 is transmitted to signal conditioner 34 and then to activity threshold detector 36. When activity is below the programmed threshold level, a binary 0 is outputted on line 40. When activity is above the programmed threshold level, a binary 1 is outputted on line 40. A binary 1 will cause sensor power control 42 to be enabled, thereby causing the battery to effectively power $pO_2$ sensor 22 and the control circuitry 28 including signal conditioner 44 and programmable modification circuit 46. The output of programmable modification circuit 46 on line 49 inputs to the pacer circuitry 19 to modify the pacer circuit 19 as appropriate.

The $pO_2$ sensor 22 monitors the partial pressure of oxygen in the blood. Feedback of the $pO_2$ levels in the blood is processed by the signal conditioner 44 and the algorithm controlled modification circuit 46. Any change in rate or escape interval of the pacing circuitry 19 is dictated by an algorithm or algorithms within the control circuit 28. If the patient's heart rate is above that which is dictated by the process signals of the $pO_2$ levels under the control of the control circuit 28, no stimulation occurs. However, if the heart rate is below the dictated rate, stimulation of the ventricle occurs at a rate determined by the processed signal. If the activity level of the patient decreases, there is a decrease in the output of the piezoelectric element 26. When the activity level drops below the programmed threshold, the sensor power control 42 is disabled, discontinuing $pO_2$ monitoring. The ventricular demand cardiac pacer returns to functioning at an output that is not controlled by the $pO_2$ levels of the blood.

Although the preferred embodiment of the present invention concerns a sensor 22 which measures the partial pressure of oxygen ($pO_2$), other sensors which measure other physiological parameters can be utilized. These may include sensing blood pressure, core temperature, $CO_2$ and $pCO_2$, $O_2$ in addition to $pO_2$, pH, respiration rate and depth (using, for example, impedance plethysmography), ventricular volume, and any other physiological change which occurs during exercise.

In a preferred embodiment, the implantable cardiac pacer 12 is a ventricular inhibited pacer (VVI). However, other types of cardiac pacers can be used such as a DDD type pacer or variations thereof.

It is seen that in the illustrative embodiment, the pacer system utilizes an activity sensor which is passive and does not require excitation, and thus does not tax the power supply heavily when the patient is inactive. Further, in the illustrative embodiment the output of the activity sensor processing circuitry is not used to set the escape interval. Instead, the output is a logic signal which indicates the presence or absence of physical activity exceeding a threshold amount. This logical signal controls the state of a physiological sensor, turning it on only when activity exceeds a predetermined level and turning it off when the patient becomes sedentary.

Such activity sensing may have applications in other areas of pacemaker control or decision-making. For example, biphasic output stages may be controlled so that compensation and evoked potential analysis (i.e., QT measurement) are enabled only during exercise. Such analysis can be extended to the control of analog to digital conversion and digital signal processing in applications which require signal analysis only during activity such as exercise. Additionally, the classification of atrial tachycardia (high atrial rate) may be "normal" (i.e., physiologic) if the activity sensor detects that the patient is active.

Although an illustrative embodiment of the invention has been shown and described, it is to be understood that various modifications and substitutions may be made by those skilled in the art without departing from the novel spirit and scope of the present invention.

What is claimed is:

1. A cardiac pacing system which comprises:
   an implantable pacer;
   passive means requiring no power for sensing the physical activity of the pacer-wearing patient;
   a physical activity threshold detector coupled to said physical activity sensing means;
   means for sensing a selected physiological parameter of the patient; and
   means for controlling the operation of said physiological parameter sensing means in response to detection of a physical activity threshold by said physical activity threshold detector.

2. A cardiac pacing system as described in claim 1, said implantable pacer including a sense amplifier for receiving sensed cardiac signals and pulse rate and timing means.

3. A cardiac pacing system as described in claim 1, including signal conditioning means coupling said passive member to said physical activity threshold detector.

4. A cardiac pacing system as described in claim 3, including means for programming said physical threshold detector for operational control at a selected threshold of physical activity.

5. A cardiac pacing system as described in claim 1, said controlling means including means for powering said physiological parameter sensing means; said controlling means being operable to enable said powering means only if a selected physical activity threshold is detected by said physical activity threshold detector.

6. A cardiac pacing system as described in claim 1, said physical activity sensing means comprising a piezoelectric element that is passive whereby no power is required to render it operational, said piezoelectric element being operative to generate a signal responsive to physical activity of the pacer-wearing patient.

7. A cardiac pacing system as described in claim 1, said physiological parameter sensing means being adapted to sense a physiological parameter from one or more of the group consisting of the partial pressure of oxygen ($pO_2$), blood pressure, core temperature, $CO_2$ and $pCO_2$, $O_2$ in addition to $pO_2$, pH, respiration rate, respiration depth, and ventricular volume.

8. A cardiac pacing system as described in claim 7, said physical activity sensing means comprising a piezoelectric element that is passive whereby no power is required to render is operational, said piezoelectric element being operative to generate a signal responsive to physical activity of the pacer-wearing patient.

9. A cardiac pacing system which comprises:
   an implantable pacer;
   said implantable pacer including a sense amplifier for receiving sensed cardiac signals and pulse rate and timing means;
   means for sensing the physical activity of the pacer-wearing patient, said physical activity sensing means comprising a passive member requiring no power carried by the implantable pacer;
   a physical activity threshold detector;
   signal conditioning means coupling said passive member to said physical activity threshold detector;
   means for programming said physical activity threshold detector for operational control at a selected threshold of physical activity;
   means for sensing a selected physiological parameter of the patient, said physiological parameter sensing means being adapted to sense a physiological parameter from one or more of the group consisting of the partial pressure of oxygen ($pO_2$), blood pressure, core temperature, $CO_2$ and $pCO_2$, $O_2$ in addition to $pO_2$, pH, respiration rate, respiration depth, and ventricular volume; and
   means for controlling the operation of said physiological parameter sensing means in response to detection of a physical activity threshold by said physical activity threshold detector, said controlling means including means for powering said physiological parameter sensing means and being operable to enable said powering means only if a selected physical activity threshold is detected by said physical activity threshold detector.

10. A cardiac pacing system as described in claim 9, said physical activity sensing means comprising a piezoelectric element that is passive whereby no power is required to render it operational, said piezoelectric element being operative to generate a signal responsive to physical activity of the pacer-wearing patient.

11. A cardiac pacing system which comprises:
    an implantable pacer;
    means for sensing cardiac activity and for transmitting cardiac activity signals to the pacer;
    means for stimulating cardiac muscle;
    said pacer including pulse generating means located inside the pacer for providing stimulating pulses to the stimulating means;
    passive means requiring no power for sensing the physical activity of the pacer-wearing patient;
    means for sensing a selected physiological parameter of the pacer-wearing patient;
    a physical activity threshold detector, coupled to said physical activity sensing means;
    means for powering said physiological parameter sensing means;
    means for inhibiting power to said physiological parameter sensing means unless said physical activity threshold detector detects at least a predetermined threshold of physical activity; and
    means for controlling the pulse generating means to vary the stimulating pulse output therefrom in response to the sensed physiological parameter.

12. A cardiac pacing system as described in claim 11, wherein said means for sensing cardiac activity, means for stimulating cardiac muscle and means for sensing a selected physiological parameter all comprise a single, unitary lead connected to the pacer.

13. A cardiac pacing system as described in claim 11, said physical activity sensing means comprising a piezoeletric element that is passive whereby no power is required to render it operational, said piezoelectric element being operative to generate a signal responsive to physical activity of the pacer-wearing patient.

14. A cardiac pacing system as described in claim 11, said physiological parameter sensing means being adapted to sense a physiological parameter from one or more of the group consisting of the partial pressure of oxygen ($pO_2$), blood pressure, core temperature, $CO_2$ and $pCO_2$, $O_2$ in addition to $pO_2$, pH, respiration rate, respiration depth, and ventricular volume.

15. A cardiac pacing system which comprises:
an implantable pacer;
means for sensing cardiac activity and for transmitting cardiac activity signals to the pacer;
means for stimulating cardiac muscle;
said pacer including pulse generating means located inside the pacer for providing stimulating pulses to the stimulating means;
means for sensing the physical activity of the pacer-wearing patient, said physical activity sensing means comprising a piezoelectric element that is carried by the implantable pacer and is passive whereby no power is required to render it operational, said piezoelectric element being operative to generate a signal responsive to physical activity of the pacer-wearing patient;
means for sensing a selected physiological parameter of the pacer-wearing patient, said physiological parameter sensing means being adapted to sense a physiological parameter from one or more of the group consisting of the partial pressure of oxygen ($pO_2$), blood pressure, core temperature, $CO_2$ and $pCO_2$, $O_2$ in addition to $pO_2$, pH respiration rate, respiration depth, and ventricular volume;
a physical activity threshold detector;
a signal conditioning means coupling said piezoelectric element to said physical activity threshold detector;
means for powering said physiological parameter sensing means;
means for inhibiting power to said physiological parameter sensing means unless said physical activity threshold detector detects at least a predetermined threshold of physical activity; and
means for controlling the pulse generating means to vary the stimulating pulse output therefrom in response to the sensed physiological parameter.

16. A physiological sensitive cardiac pacing process which comprises the steps of:
providing an implantable pacer;
sensing the physical activity of the pacer-wearing patient by a passive element requiring no power;
sensing a selected physiological parameter of the patient;
detecting a selected threshold of the patient's physical activity; and
controlling the physiological sensing in response to detection of the selected physical activity threshold.

17. A physiological sensitive cardiac pacing process as described in claim 16, wherein the step of sensing the selected physiological parameter includes the steps of sensing a physiological parameter from one or more of the group consisting of the partial pressure of oxygen ($pO_2$), blood pressure, core temperature, $CO_2$ and $pCO_2$, $O_2$ in addition to $pO_2$, pH, respiration rate, respiration depth, and ventricular volume.

18. A physiological sensitive cardiac pacing process which comprises the steps of:
providing an implantable pacer;
sensing cardiac activity and transmitting cardiac activity signals to the implantable pacer;
providing stimulating pulses for stimulating the cardiac muscle;
sensing the physical activity of the pacer-wearing patient by a passive element requiring no power;
sensing a selected physiological parameter of the pacer-wearing patient; and
inhibiting power to said means for sensing the physiological parameter unless the physical activity that is sensed is at least a predetermined physical activity threshold.

* * * * *